(12) United States Patent
Vurens et al.

(10) Patent No.: US 7,206,066 B2
(45) Date of Patent: Apr. 17, 2007

(54) REFLECTANCE SURFACE ANALYZER

(75) Inventors: Gerard H. Vurens, Santa Clara County, CA (US); Kasra Khazeni, Santa Clara County, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 345 days.

(21) Appl. No.: 10/804,926

(22) Filed: Mar. 19, 2004

(65) Prior Publication Data

US 2005/0206884 A1 Sep. 22, 2005

(51) Int. Cl.
*G01N 21/88* (2006.01)

(52) U.S. Cl. .................................. 356/237.2; 356/369

(58) Field of Classification Search ................ 356/369, 356/237.2, 236, 237.1, 630–632; 250/225, 250/228, 559.4, 559.41, 599.45; 350/559.45
See application file for complete search history.

(56) References Cited

U.S. PATENT DOCUMENTS

| | | | |
|---|---|---|---|
| 4,585,348 A | 4/1986 | Chastang et al. | |
| 4,681,450 A | 7/1987 | Azzam | |
| 4,872,758 A | 10/1989 | Miyazaki et al. | |
| 4,893,932 A | 1/1990 | Knollenberg | |
| 4,908,508 A | 3/1990 | Dubbeldam | |
| 5,076,696 A * | 12/1991 | Cohn et al. ................. | 356/369 |
| 5,102,222 A | 4/1992 | Berger et al. | |
| 5,282,217 A | 1/1994 | Yamazaki | |
| 5,311,285 A | 5/1994 | Oshige et al. | |
| 5,335,066 A | 8/1994 | Yamada et al. | |
| 5,438,415 A | 8/1995 | Kazama et al. | |
| 5,517,312 A | 5/1996 | Finarov | |
| 5,644,562 A | 7/1997 | De Groot | |
| 5,726,455 A | 3/1998 | Vurens | |
| 5,790,259 A | 8/1998 | Mizuhata et al. | |
| 5,835,220 A | 11/1998 | Kazama et al. | |
| 6,088,092 A | 7/2000 | Chen et al. | |
| 6,134,011 A | 10/2000 | Klien et al. | |
| 6,307,627 B1 * | 10/2001 | Vurens ........................ | 356/369 |
| 6,384,910 B2 | 5/2002 | Vaez-Iravani et al. | |
| 6,483,586 B1 * | 11/2002 | Johs et al. .................. | 356/369 |
| 6,515,745 B2 | 2/2003 | Vurens et al. | |
| 6,859,278 B1 * | 2/2005 | Johs et al. .................. | 356/369 |
| 7,002,675 B2 * | 2/2006 | MacGibbon et al. ...... | 356/237.2 |

OTHER PUBLICATIONS

Azzam R.M.A. "Ellipsometry" Handbook of Optics: Devices, Measurements & Properties vol. II, 2nd Edition, Bass, M. et al.(eds). McGraw Hill, Inc.: Chapter 27, pp. 27-1-27.26 (1995).

Meeks, S. et al. "Optical Surface Analysis of the Head-Disk-Interface of Thin Film Disks" Transactions of the ASME, presented Oct. 1994, Maui, HI.

(Continued)

*Primary Examiner*—Gregory J. Toatley, Jr.
*Assistant Examiner*—Marissa J. Detschel
(74) *Attorney, Agent, or Firm*—Caven & Aghevli LLC (57) ABSTRACT

There is described an improved Surface Reflectance Instrument which achieves more complete detection of surface defects in the nature of small particles. One of the improvements is the use of an elliptical integrated cavity with internal surface mirrors, and another the use of a position sensing diode as the detector for the scattered light. Other improvements and the use of a stable laser at a particular wavelength resulting in greater detection are also described.

19 Claims, 5 Drawing Sheets

OTHER PUBLICATIONS

Bright, D. et al. "Concentration histogram imaging: a quantitative view of related images" Microscopy: The Key Research Toll, Mar. 1992, pp. 21-28.

Klein, D. et al. "Measurements of Thin Film Disks by Surface Reflectance Analysis" SPIE Conference on Surface Characterization for Computer Disks, Wafers and Flat Panel Displays, San Jose, CA Jan. 1999, vol. 3619, pp. 18-26.

Optics, Miles V. Klein and Thomas E. Furtak, Second Edition, Wiley, pp. 134-135.

Miles V. Klein and Thomas E. Furtak, Optics & Laser Physics, Second Edition, Apr., 1986, pp. 134-135, Wiley.

Michael Bass, Handbook of Optics, Second Edition, vol. II, 1995, pp. 27.1, 27.15-17, 27.25, and 27.26, McGraw Hill, Inc.

David L. Klein, Gerard H. Vurens, Measurements of Thin Film Disks by Surface Reflectance Analysis, Surface Characterization for Computer Disks, Wafers, and Flat Panel Displays, Jan. 28, 1999, pp. 18-26, vol. 3619, The Society of Photo-Optical Instrumentation Engineers, San Jose, California, USA.

* cited by examiner

REFLECTANCE SURFACE ANALYZER

BACKGROUND OF THE INVENTION

This invention relates to optical instrumentation and to the optical measurement of surface qualities and characteristics. In particular there exists today instruments to study surfaces by reflective techniques. These provide measurements of various characteristics and/or qualities of surfaces and of thin film layers that are at least partially light transmissive when deposited on a substrate. A surface for measurement may comprise the surface of a hard disk or a computer memory which initially may comprise a metallic or glass support layer and deposited coating layers of magnetic media with a final layer of carbon and a lubricant layer deposited onto the surface of the disk on the carbon layer.

One form of instrument for optical diagnostics is known as a reflection ellipsometer. Another is known as a polarization-modulated ellipsometer. However, these units are relatively slow and not useful in situations demanding real time measurements of a sample including large amounts of data.

An instrument that can be used for real time detection and analysis is called a Surface Reflectance Analyzer. It is capable of optically scanning the entire surface of a sample providing measurement data and visual images of a wide range of surface properties in a matter of seconds. It provides real time access to large amounts of data that define surfaces and layer characteristics. Such an instrument is described, for example, in U.S. Pat. No. 6,307,627, and such instruments are sold by HDI Instrumentation of Santa Clara, Calif. It is this type of instrument to which the improvements of the invention are directed.

Surface Reflectance Analyzers use an intensity stabilized light source that is directed to and reflected from a surface being studied. It provides in a single scan sufficient data as to enable a comprehensive and a sophisticated analysis. The system may measure three or more sample related parameters simultaneously. In practice, the specularly reflected light beam from the surface being studied is converted into its s and p polar components for measurement purposes. At least a third component is also typically measured simultaneously, which may for example be the scattered light from the surface. Modern equipment uses an integrating sphere to pick up, gather, and detect the scattered light. Such a structure for example is shown in FIG. 2 of U.S. Pat. No. 6,134,011. This same patent also describes the use of a laser which today typically appears in commercial units. It produces a stable output at 670 nm. Since all measurements are made simultaneously, real time measurements and determinations of desired parameters can and become available immediately. The instrument may be used, for example, in studies of hard memory disks for computer systems, semiconductor layers, photonics and surfaces used in medical applications. In operation, one can create, in a single pass, a map of the entire surface being examined as to show residues, scratches, waviness, particles, film thickness uniformity, etc. For example in working with a computer disk following a polishing operation in the manufacture of the disk, one can determine whether the surface finish meets the requirements for the product. The instrument may also be used for the measurement of the thickness and other characteristics of a deposited coating and can visually display surface smoothness, waviness and uniformity variations, among other things. Thus one has the capability, for example, of simultaneously analyzing p polar, s polar, Phase Contrast, Scattered, Circumferential and Radial parameters in seconds in studying a surface or layer.

SUMMARY OF THE INVENTION

As more is demanded from units such as hard disks and other products with which the present instrumentation is used, more is required from the instrumentation since the instruments themselves must be capable of detecting more information and information of a more sensitive nature. Current instrumentation is very effective in showing gradual surface variations such as waviness, gradual changes in thickness or optical characteristics in a thin film layer. Yet greater sensitivity is required in connection with the detection of surface scratches as well as the detection of smaller scattering events such as those produced by small particles. In this respect, improving techniques for the detection of scattered light by Surface Reflectance Analyzers is recognized as a mechanism to enhance the detection of surface scratches as well as other scattering events such as small particles at the surface or in the uppermost layer. This invention permits the acquisition of greater amounts of useful data from the surface or layer under examination than has heretofore been possible through improvements in, among other segments, the detection system of the instrument. This also includes the capability of determining the directionality and the spatial distribution of scattered light from the surface or layer under examination. Also to assure the dependability of manufactured instrumentation, certain optical and structural elements have been incorporated into the units, such as compensators and other assemblies that permit flexibility in positioning components. These elements enable fine tuning as well as adjustments in the final product so that each manufactured unit will regularly be of the highest quality notwithstanding slight variations that typically exist from like parts as would normally get incorporated into successive units of equipment during manufacture.

According to Rayleigh's scattering theory, scattering cross section of a small spherical particle of radius a, by photons of wavelength $\lambda$, provided $a<<\lambda$, is proportional to:

$$a^6/\lambda^4$$

Therefore in order to detect smaller scattering events such as those produced by small particles, lasers with smaller wavelengths are beneficial. Additionally, efficient collection of scattered light from the surface being measured is essential. Currently an integrating sphere is used, in which scattered light is collected using a spherical cavity with a diffused white surface on the inside. The sphere is positioned above but close to the surface where the laser beam is focused to strike. Any scattering event on the surface being examined produces scattered light that is captured by the cavity. Within the cavity, the light bounces off the inside walls many times and finally is picked up at a detector located at the other end of the cavity. A problem with this type of integrating cavity is that they are not very efficient. In order to detect as much of the scattered light as possible or in order to act with greater efficiency Surface Reflectance Analyzers in accordance with this invention use a newly designed cavity that is much more efficient and is thus more effective in detecting scattering light events or incidents at the surface under examination. The novel cavity in accordance with this invention has a mirror or mirror-like finish on its inside surface walls and is more efficient in gathering and detecting data.

It is accordingly an object of this invention to describe an improved Surface Reflectance Analyzer capable of producing more information than has heretofore been possible as to improve the output information of such instrumentation.

It is a further object of this invention to describe a novel integrating cavity with an elliptical configuration which efficiently gathers and detects incoming signals of surface faults.

It is a further object of this invention to describe an improved Surface Reflectance Analyzer employing a stabilized laser of reduced frequency which will enhance the detection of surface scatter and surface information.

These and other objects and benefits will become apparent in connection with the more complete description of these improvements in the following material.

DETAILED DESCRIPTION

Figure 1:
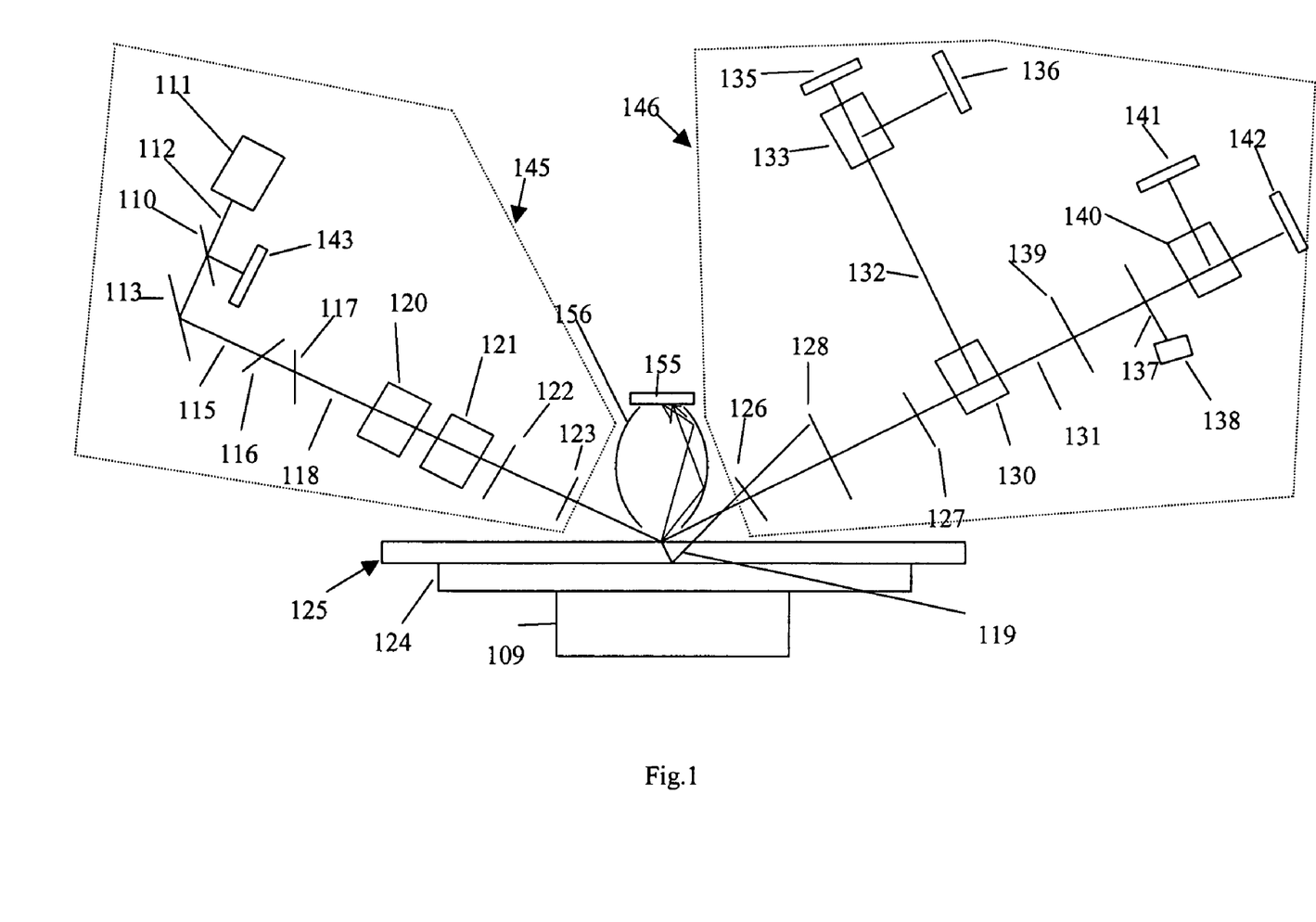
FIG. 1 is a schematic side view illustrating the optical instrument of this invention.

Referring now to FIG. 1, a light source 111 directs a beam illustrated as 112 through a beamsplitter 110 and a detector 143 to monitor the laser power. The beam is then directed onto a mirror 113 where it is reflected as beam 115 (different numbers are being used in connection with different sections of the beam in order to simplify understanding of the drawings). The mirror is positioned on a mirror mount to steer the beam so that it eventually strikes the surface under examination at an angle of approximately sixty degrees. The mirror 113 permits use of a folded optical system that has the effect of shortening its length. However, if the overall length of the system is not important, the mirror could be omitted. The angle of incident although not unique, is chosen to fall within the range of 50 & 80 degrees from the normal. The beam next passes through filters 116 and 117. These are neutral density filters placed at an angle other than normal to the beam and in an opposite sense one to the other. The filters may be omitted from the structure depending on the desired intensity of the beam at the surface or depending on the intensity of the laser. The filters, if used, and if used in a tilted configuration, first reduce the intensity of the beam and further prevent reflected portions of the beam from reaching the light source, which could make the source unstable. The different angles selected for the filters relative to each other and with respect to the beam cancel the effect of filter thickness on path displacement. The beam following the filters is identified as 118. A single filter could also be used. This would result in an offset of the beam that could be compensated for, by an adjustment in the mirror position.

After the filters, the beam goes through beam expander 120 where the beam diameter is increased. It then passes through a high efficiency circular polarizer 121 and then through a linear polarizer 122. It next continues through focusing optics which in this instance, as well as other instances in the structure of this equipment, may comprise one or more lenses 123, which focus the beam to impinge onto the surface 125 being examined. Optics are selected such that the spot size on the surface is a minimum and is diffraction limited. In this embodiment the substrate 125 is rotated at a high speed during the period that information is being gathered.

The light reflected from the surface under examination is then passed through a lens system 126 illustrated as a collecting lens which focuses the beam some 3 to 4 centimeters away from the surface (the scattered part of the beam off the surface will be discussed later). At the point of refocus, filter 128 which includes a pin-hole in a mask is positioned and acts to block unwanted reflection from the bottom surface of the substrate in the nature of secondary reflections 119 in case of a substrate that is partially or completely transparent at the beam wavelength. In FIG. 1 this is illustrated by the light path 119 shown extending from the base of the substrate 125 and striking the upper edge portion of filter 128. The pinhole in this instance is not positioned to block the reflections that occur a few microns from the surface under inspection even though such reflections are from the bottom of a thin transparent film layer overlying the surface. The pinhole is mounted on an xy translation stage to simplify alignment and can be positioned as to focus at a selected surface.

After that the beam passes through another lens or optical system 127 where the beam is collimated. It then passes through a 50/50 non-polarizing beam splitter 130 that splits the beam into two nearly equal intensity beams 131 and 132 separated by 90 degrees. The equal intensity separation is not necessary but only convenient. This splitting of the beam introduces an unwanted phase shift between the s and p polar components of both the transmitted and the reflected portions of the light. In the reflected portion the magnitudes of the p and s polar components are of primary interest. Beam 132 is then passed through a beam splitting polarizer 133. Polarizer 133 which may for example comprise a Glan Thompson prism spatially separates the s-polar component of the beam from its p-polar component. Thereafter, the intensities of the s-polar and the p-polar components are separately measured by two different photo-detectors or photodiodes 135 and 136. In the transmitted portion the unwanted phase shift between the s and p polarizations is compensated for since it is desired to measure the phase shift caused by the surface under investigation. This may be achieved using compensator 139 which may for example comprise a Berek's Compensator. A compensator is an optical unit designed to retard one of the beams, the s or the p polarization beam, with respect to the other to compensate for the unwanted phase shifts introduced by other optical components; therefore, any other compensator can be used to achieve the same result such as a Brace-Kohler or a Babinet compensator. The beam then goes through a wave-plate 137 that, in this case, is a quarter wave-plate. The hard axis of the quarter wave plate is placed at an angle of 45 degrees with respect to the p-polarization direction. It is also mounted on a tilting plate 138 that will allow for tilting of the wave-plate with respect to the beam axis. Tilting plate 138 is designed to tilt the wave-plate in the direction of easy and hard axes. The retardation caused by the wave-plate is a function of these tilting angles. This permits tuning of the retardation. The beam will then pass through another beam splitting polarizer 140 which again may comprise a Glan Thomson prism and the two outputs are again measured with two different photodiodes 141 and 142. These outputs are used to calculate the phase difference between the s and p polarized components of the reflected light caused by the surface under investigation to provide phase shift measurements using this instrument.

The illumination portion of the system 145 shown in FIG. 1 comprises the elements starting at the light source 111 and continuing through optics 123 to the point where the beam that passes through lens 123 strikes surface 125. It is movably suspended on a track or stage for one dimensional translation motion along an axis perpendicular to the plane of the paper over base 124. The detection system 146, of the instrument comprising the elements starting with the optics 126 and extending through the photo detectors 135, 136, 141, and 142, is also movably supported on a track or stage which is the same track or stage as supports the illumination portion 145. This is clear on considering FIG. 4 hereinafter. This support system provides one dimensional translation motion along radial direction with respect to the rotation axis of the turntable 124. Either the optics moves along this axis with respect to the turntable or the turntable moves with respect to the optics. In either case the sample is being rotated on the turntable.

The preferred light source 111 in accordance with this invention is a diode pumped solid state laser operating at a wavelength of 532 nm. Such a laser is compact and fits the optical system described without requiring enlargement. This laser emits a green light. In general, a laser with a relatively short wavelength is preferred in systems in which scattered light is used in the measurements since the intensity of the scattered light is proportional to the inverse of the wavelength to the power of four. Thus such a laser creates an instrument that is more sensitive for detecting smaller particles on the surface. This preferred laser may be purchased from BW Tek or from Crystal Laser Corporation. It also has the benefit of providing a smaller diameter light beam and is stable which in turn improves the output of image information. It should be understood however, that depending on the system in use, various other lasers would also operate well in achieving the objectives of this invention. The green laser described is preferred because measuring with certain wavelengths, for example, in the blue/violet may damage samples that are biological or of certain organics materials. In applications where samples are more robust smaller wavelengths make the measurements more sensitive to scattering events and to detection from thinner films. For a general purpose instrument the laser may be substantially any wavelength. If the object is to avoid damaging samples that may include biological or organic materials it is generally preferred to work with wavelengths above about 400 nm. However, it should be understood that the elliptical cavity to be discussed below can and will effectively and efficiently function to improve detection of scattered light from the surface under study whatever the wavelength of the laser of the system. As indicated above however, the lower the wavelength of the laser, the more the system will detect surface anomalies and the scattered light from the surface.

The substrate 125 being examined is supported on test stand or turntable 124, driven by an air bearing mechanism and control electronics 109. The driver and control electronics cause turntable 124 to rotate at a selected speed in the range of 100–30,000 RPM. This is shown in more detail in FIG. 2.

Figure 2:
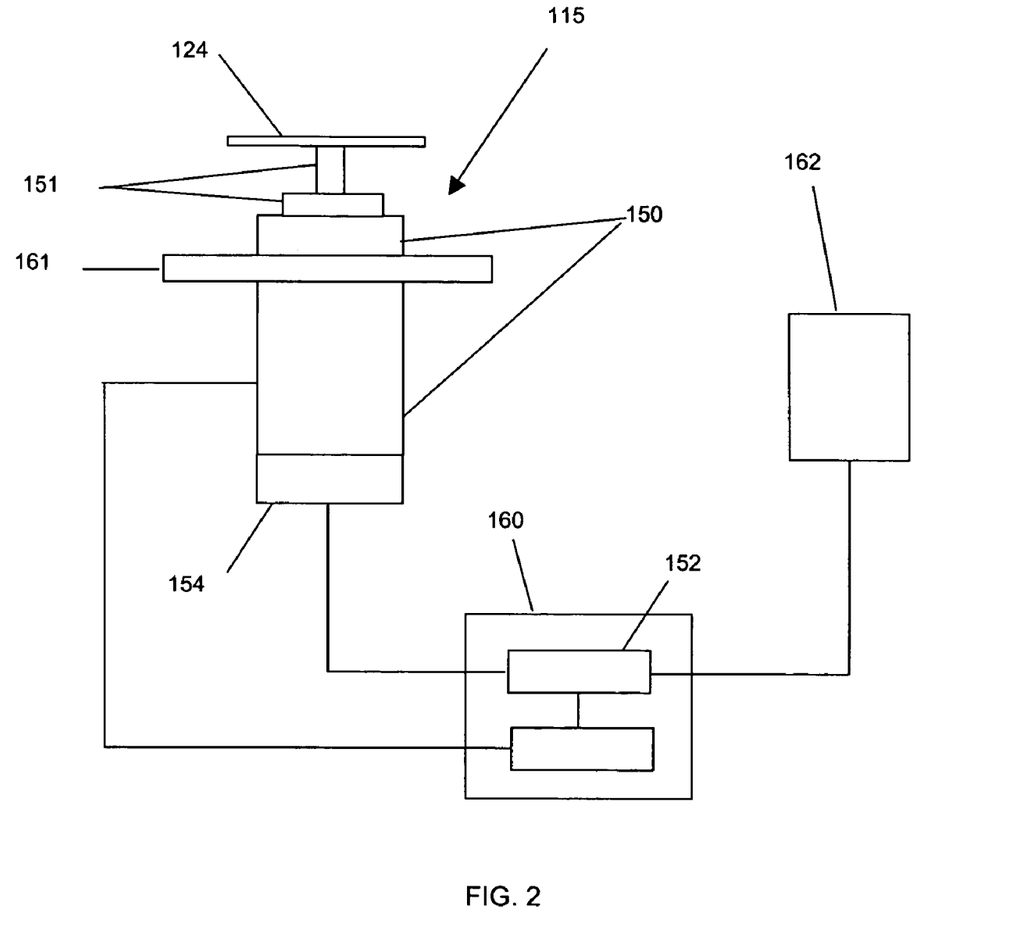
FIG. 2 is a schematic view of the test stand and the control electronics.

Referring now to FIG. 2, turntable 124 is positioned on drive system 109 and motor 150 and turntable 124. The drive system may comprise an air bearing 151. Motor 150 is held in position by mounting plate 161. A rotary encoder 154 determines angular positions and signals correspondingly to monitor 152 which is incorporated into control electronics 160. In turn control electronics 160 connects to and feeds status and data information into CPU 162. Rotation of turntable 124 is commanded by the CPU 162 as controlled by the control electronics 160. Other parts of the system including the photo-detectors 155, 135, 136, 141, and 142 shown in FIG. 1 are also connected to CPU 162 and each feeds signals to the CPU where they are continuously monitored or controlled and from which collected data is fed to produce image information concerning the surface being studied. It should be mentioned that one or all of the detectors 135, 136, 141, 142, and 155 can be position sensing photo-detectors. A position sensing photo-detector is comprised of more than one photo-detector made on the same semiconductor chip very close to each other in various configurations. If a so-called quadrant photo-diode is used instead of any or all of the detectors 135, 136, 141, and 142, the variations in the reflected angle can be measured. If a quadrant or any other position sensing photo-diode is used in place of detector 155, then the directionality of the scattered light from the surface can be deduced which can indicate and differentiate between various scattering defects such as shape of particles, scratches, etc.

Also shown in FIG. 1 is cavity 156 positioned at the point of focus of the incoming light beam striking the surface under examination. This is shown in greater detail in FIG. 3. Positioned at the top of this cavity is photo-detector 155. The cavity and detector in concert measure scattered light from the surface under examination. The cavity is in the shape of an ellipsoid. It includes mirrors or mirror like surfaces along its internal walls. These mirror surfaces result in the capture of substantially all of the signals entering the elliptical integrating cavity. This considerably increases the sensitivity of the instrument in detecting surface particles and other surface anomalies in the detected scattered light. Using the elliptical integrated cavity any scattered light from the surface, no matter which direction it scatters, will end up on the detector element of the photodiode. This will increase the signal to noise ratio as none of the signal is left undetected, limited by the angle of acceptance of the ellipsoidal cavity. The angle of acceptance is structurally large since the cavity is positioned very close to the surface of the sample under study.

Figure 3:
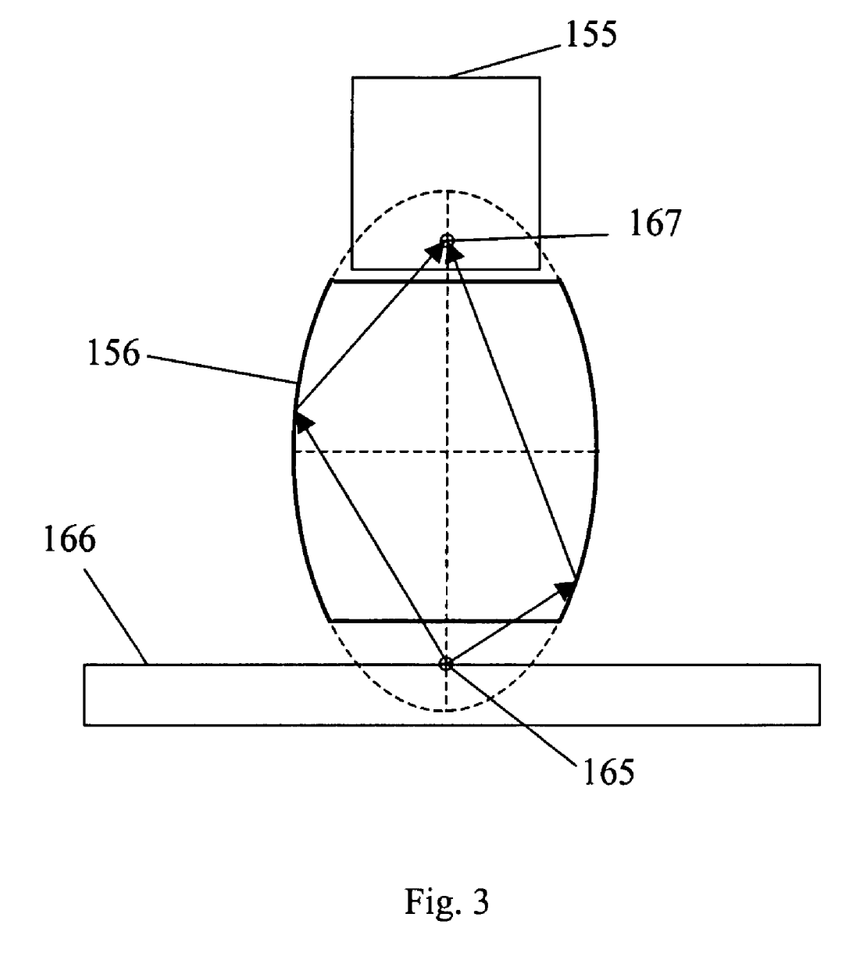
FIG. 3 is a schematic side view of the novel cavity as it relates to the surface under study.

The dimensions of the ellipse are really not relevant. What is critical is to engineer and position this cavity such that its two focal points are carefully positioned. Thus the lower focal point should be as illustrated at 165 substantially coinciding with the surface under study 166. The other focal point 167 is positioned to coincide with the surface of detector 155. The dashed lines at the upper and lower ends show the complete mathematical ellipse with its major and minor axes. The actual elliptical cavity used in the instrument described is truncated at the top and bottom since these portions of the ellipsoid would obviously interfere with the surface under examination and the surface of the detector. The arrows within the cavity illustrate how scattered light from the surface under examination is reflected and focused onto the detector in this figure at the upper end of the elliptical cavity. In general the smaller the unit the smaller the packaging for the system. The design used in constructing the instrument illustrated is about 1 inch by 0.5 inch.

Figure 4:
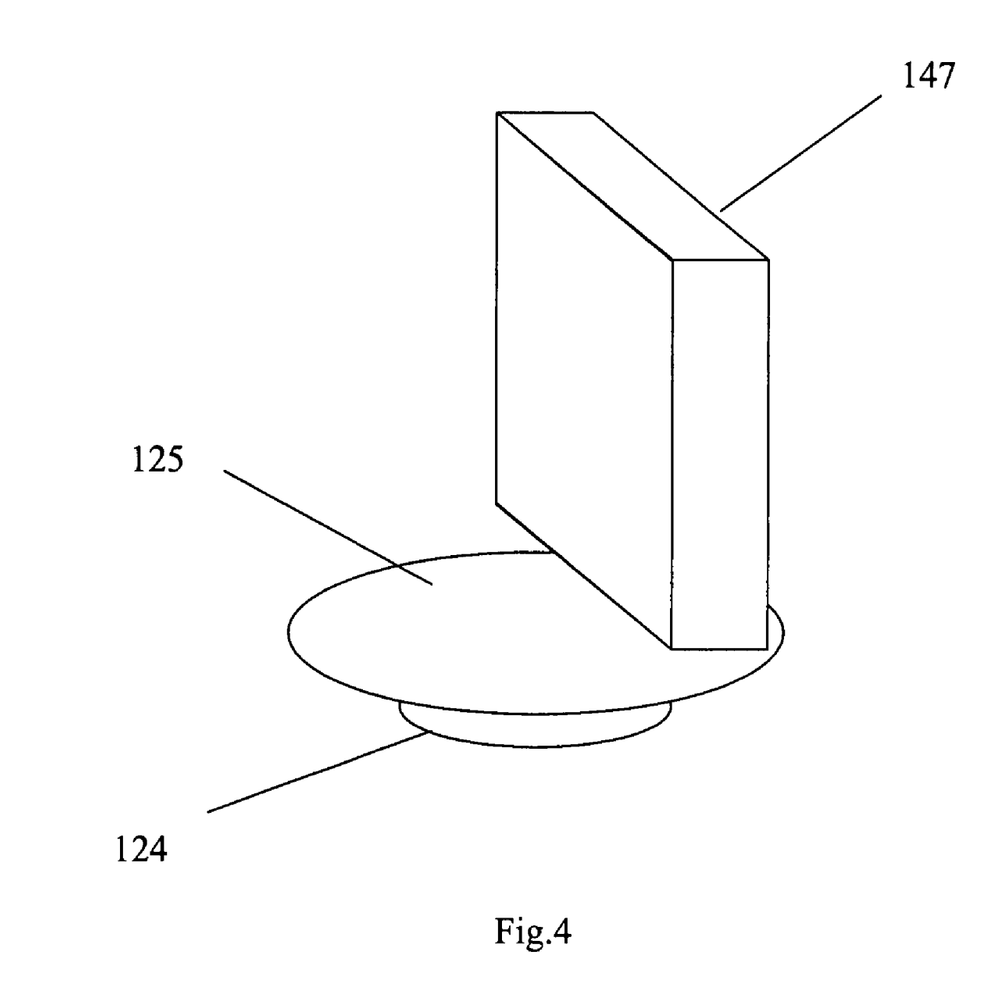
FIG. 4 is a schematic illustrating the different ways data may be gathered from a disk; and, FIG. 5 is a schematic of a quadrant photo detector that may be used with this invention.

Referring now to FIG. 4, this Figure is intended to simplify the explanation of how the optics is moved relative to the surface under examination in order to gather information. Illustrated in this Figure is optics package 147, which may comprise both an illumination and a detection system (see 145 and 146 in FIG. 1), on a moving stage positioned above the surface of the disk 125 located on base 124. In each of the embodiments illustrated by this Figure the disk 125 is in rotational motion. In one embodiment the optics package is moved from the left or the right side of this illustration to the right across the surface of disk 125. In a second embodiment, the optics package 147 is stationary and the disk support 124 with a disk in place is itself moved under the optics package. In this case the disk would be moved toward the left or the right side of the drawing.

Figure 5:
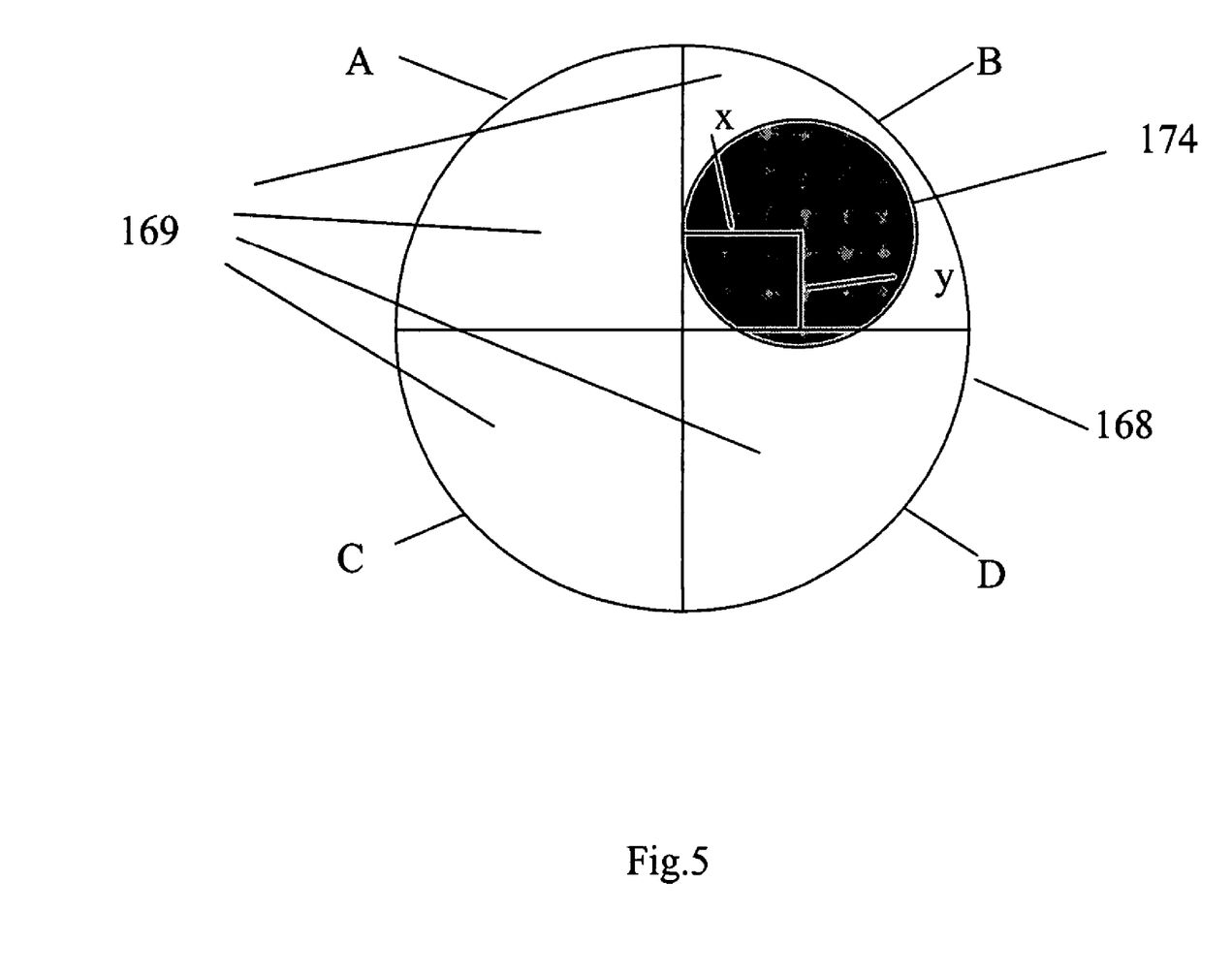

Referring now to FIG. 5, there is illustrated a position sensing diode arrangement 168 comprising four diodes 169 arranged forming a circle. The illustrated diode is a quadrant photo-diode. Although other diode arrangements can be used the quadrant photo-diode is preferred. The rough coordinate (x, y) of a spot of light, 174, on this arrangement can be calculated from the following equations:

$$y=((IA+IB)-(IC+ID))/(IA+IB+ID+IC)$$

$$x=((IB+ID)-(IA+IC))/(IA+IB+ID+IC)$$

where IA, IB, IC, and ID are the photo-currents measured form diodes A, B, C, and D respectively.

As it has been mentioned, if this kind of photo-diode is used instead of any or all of the detectors 135, 136, 141, and 142, the variations in the reflected angle being detected by the detector can be measured. If it is used in place of detector 155, then the directionality of the scattered light from the surface can be deduced which can indicate and differentiate between various scattering defects such as shape of particles, scratches, etc.

While there has been shown and discussed what are presently considered the preferred embodiments, it will be obvious to those skilled in this art that various changes and modifications may be made without departing from the scope of this invention and the coverage of the appended claims.

What is claimed is:

1. An optical measuring system for evaluating a substrate, the system comprising
    a laser configured to generate an intensity stabilized light beam;
    an optical system for directing the beam to a spot on a substrate being evaluated;
    drive mechanism to rotate the substrate;
    track and support structures to bring about relative motion of the light beam relative to the surface of the substrate as the substrate rotates;
    a detection system configured to receive and detect light reflected from the substrate;
    said detection system including polarizers to convert the reflected beam to s and p polarized light and detectors to read the information content of the s and p polarized reflected beams; and,
    an elliptical cavity positioned adjacent to the point of impingement by the beam onto the substrate to capture the scattered light from the substrate and to detect the information incorporated into the detected scattered light to provide surface information of the substrate under evaluation.

2. An optical measuring system in accordance with claim 1 in which a focal point of said elliptical cavity is positioned substantially at the surface being examined.

3. An optical measuring system in accordance with claim 1 in which a detector is positioned substantially at a focal point of said elliptical cavity.

4. The optical measuring system of claim 1 in which the laser generates an intensity stabilized wavelength of approximately 532 nm.

5. The optical measuring system of claim 4 in which said elliptical cavity is positioned with a focal point substantially at the surface under examination and the other focal point at the detector for said cavity.

6. The optical measuring system of claim 1 in which said detection system includes a beam splitter to split the reflected beam into two paths and to convert the second split beam into s and p polarized beams.

7. The optical measuring system of claim 1 in which said elliptical cavity has internal reflecting surfaces to effectively detect substantially all the scattered light of the optical measuring system entering the elliptical cavity.

8. The optical measuring system of claim 1 in which said elliptical cavity is positioned with a focal point substantially at the surface under examination and the other focal point of said cavity substantially at the detector.

9. An optical system in accordance with claim 1 in which one or more of the detectors comprises a position sensitive photo-detector.

10. The optical system of claim 9 in which said photo-detectors comprise quadrant photo-diodes.

11. An optical measuring system for evaluating a substrate, the system comprising
    a laser configured to generate an intensity stabilized light beam in a wavelength of above about 400 nm;
    an optical system for directing the beam to a particular spot on a substrate being evaluated;
    drive mechanism to rotate the substrate;
    track and support structures to bring about relative motion of the light beam relative to the surface of the substrate as the substrate rotates;
    a detection system configured to receive and detect light reflected from the substrate;
    said detection system including polarizers to convert the reflected beam to s and p polarized light and detectors to read the information content of the s and p polarized reflected beams; and,
    an elliptical cavity positioned adjacent to the point of impingement by the beam onto the substrate to capture the scattered light from the substrate and to detect the information incorporated into the detected scattered light to provide surface information of the substrate under evaluation.

12. An optical measuring system in accordance with claim 11 in which said intensity stabilized light is at 532 nm.

13. An optical system in accordance with claim 11 in which the detection system includes one or more position sensitive photo-detectors.

14. An elliptical cavity assembly for the detection of surface scattered light in a surface reflectance analyzer, comprising a truncated elliptical cavity to be positioned with the surface under examination substantially at one focal point of the cavity and a detector at the other focal point of the cavity, mirror like walls internally along the inner surfaces of the cavity, and a quarter wave plate at a tilting angle that permits tilting of the wave plate with respect to a beam axis.

15. An optical measuring system for evaluating a substrate, the system comprising
    a laser configured to generate an intensity stabilized light beam in a wavelength of above about 400 nm;
    an optical system for directing the beam to a particular spot on a substrate being evaluated;

drive mechanism to rotate the substrate;

track and support structures to bring about relative motion of the light beam relative to the surface of the substrate as the substrate rotates;

a detection system configured to receive and detect light reflected from the substrate;

said detection system including position sensitive photo-detectors to read information concerning the substrate from the substrate under evaluation; and a quarter wave plate at a tilting angle that permits tilting of the wave plate with respect to an axis of the beam.

16. An optical measuring system for evaluating a substrate, the system comprising a laser configured to generate an intensity stabilized light beam in a wavelength of above about 400 nm;

an optical system for directing the beam to a particular spot on a substrate being evaluated;

drive mechanism to rotate the substrate;

track and support structures to bring about relative motion of the light beam relative to the surface of the substrate as the substrate rotates;

a detection system configured to receive and detect light reflected from the substrate;

said detection system including quadrant photo-diodes to read information concerning the substrate from the substrate under evaluation including the directionality of the reflected light; and a quarter wave plate at a tilting angle that permits tilting of the wave plate with respect to an axis of the beam.

17. An optical measuring system for evaluating a substrate, the system comprising:

a laser configured to generate an intensity stabilized light beam;

an optical system for directing the beam to a spot on a substrate being evaluated;

drive mechanism to rotate the substrate;

track and support structures to bring about relative motion of the light beam relative to the surface of the substrate as the substrate rotates;

a detection system configured to receive and detect light reflected from the substrate;

said detection system including polarizers to convert the reflected beam to s and p polarized light and detectors to read the information content of the s and p polarized reflected beams;

compensators to compensate for unwanted phase shifts between the s and p beams introduced by other optical components; and an elliptical cavity positioned adjacent to the point of impingement by the beam onto the substrate to capture the scattered light from the substrate and to detect the information incorporated into the detected scattered light to provide surface information of the substrate under evaluation.

18. An optical measuring system for evaluating a substrate, the system comprising a laser configured to generate an intensity stabilized light beam;

an optical system for directing the beam to a spot on a substrate being evaluated;

drive mechanism to rotate the substrate;

track and support structures to bring about relative motion of the light beam relative to the surface of the substrate as the substrate rotates;

a detection system configured to receive and detect light reflected from the substrate;

said detection system including polarizers to convert the reflected beam to s and p polarized light and detectors to read the information content of the s and p polarized reflected beams; and a quarter wave plate at an angle of approximately 45 degrees with respect to the p-polarization axis on a tilting plate that permits tilting of the wave-plate with respect to the beam axis.

19. The optical measuring system of claim 18 including an elliptical cavity positioned adjacent to the point of impingement by the beam onto the substrate to capture the scattered light from the substrate and to detect the information incorporated into the detected scattered light to provide surface information of the substrate under evaluation.

* * * * *